(12) United States Patent
Zhao et al.

(10) Patent No.: US 11,262,229 B2
(45) Date of Patent: Mar. 1, 2022

(54) INSTRUMENT CALIBRATION DEVICE AND CALIBRATION METHOD USING SAME

(71) Applicant: Beijing Const Instruments Technology Inc., Beijing (CN)

(72) Inventors: Shichun Zhao, Beijing (CN); Lijun Dong, Beijing (CN); Baoqi Liu, Beijing (CN)

(73) Assignee: Beijing Const Instruments Technology Inc.

( * ) Notice: Subject to any disclaimer, the term of this patent is extended or adjusted under 35 U.S.C. 154(b) by 237 days.

(21) Appl. No.: 16/476,473

(22) PCT Filed: Aug. 22, 2017

(86) PCT No.: PCT/CN2017/098458
§ 371 (c)(1),
(2) Date: Jul. 8, 2019

(87) PCT Pub. No.: WO2018/129925
PCT Pub. Date: Jul. 19, 2018

(65) Prior Publication Data
US 2020/0319012 A1 Oct. 8, 2020

(30) Foreign Application Priority Data

Jan. 10, 2017 (CN) .......................... 201710017182.7
Jan. 10, 2017 (CN) .......................... 201720028892.5

(51) Int. Cl.
*G01F 25/00* (2006.01)
*G01F 1/36* (2006.01)
(Continued)

(52) U.S. Cl.
CPC ............ *G01F 25/0007* (2013.01); *G01F 1/36* (2013.01); *G01N 21/45* (2013.01);
(Continued)

(58) Field of Classification Search
CPC ........ G01F 25/0007; G01F 1/36; G01F 25/00; G01N 21/45; G01N 2201/127; F16K 37/00; G01D 18/00
See application file for complete search history.

(56) References Cited

U.S. PATENT DOCUMENTS 6,594,602 B1 * 7/2003 Schultz .................. G01D 3/022
702/104
2008/0110236 A1 5/2008 Hajishah et al.
(Continued)

FOREIGN PATENT DOCUMENTS

CN 2036278 U 4/1989
CN 2695936 Y * 4/2005
(Continued)

OTHER PUBLICATIONS

Extended European Search Report including Written Opinion for EP17891430.5 dated Oct. 1, 2020; 9 pages.
(Continued)

*Primary Examiner* — Peter J Macchiarolo
*Assistant Examiner* — John M Royston
(74) *Attorney, Agent, or Firm* — Lerner, David, Littenberg, Krumholz & Mentlik, LLP

(57) ABSTRACT

An instrument calibration apparatus and a calibration method using same. The apparatus comprises a physical quantity input/output unit, a physical quantity measurement unit, a physical quantity configuration unit, a display unit, a man-machine interaction unit, a storage unit, and a control unit. The apparatus can be widely applied to automatic calibration of multivariable instruments.

14 Claims, 6 Drawing Sheets

(51) Int. Cl.
*G01N 21/45* (2006.01)
*G01N 33/00* (2006.01)
*F16K 37/00* (2006.01)

(52) U.S. Cl.
CPC .......... *G01N 33/0047* (2013.01); *F16K 37/00* (2013.01); *G01N 2201/127* (2013.01)

(56) References Cited

U.S. PATENT DOCUMENTS

| | | |
|---|---|---|
| 2015/0134289 A1 | 5/2015 | Mrvaljevic et al. |
| 2016/0061349 A1* | 3/2016 | Shields ............... F16K 37/0083 702/114 |
| 2016/0104284 A1* | 4/2016 | Maguire ............ H04N 1/00172 348/187 |

FOREIGN PATENT DOCUMENTS

| | | |
|---|---|---|
| CN | 2695936 Y | 4/2005 |
| CN | 103090918 A | 5/2013 |
| CN | 204788450 U | 11/2015 |
| CN | 106767989 A | 5/2017 |
| JP | 3483632 B2 | 1/2004 |
| KR | 101606497 B1 | 3/2016 |

OTHER PUBLICATIONS

International Search Report PCT/CN2017/098458, dated Nov. 27, 2017.

* cited by examiner

INSTRUMENT CALIBRATION DEVICE AND CALIBRATION METHOD USING SAME

CROSS REFERENCE TO RELATED APPLICATIONS

The present application is a national phase entry under 35 U.S.C. § 371 of International Application PCT/CN2017/098458 filed Aug. 22, 2017, published in Chinese, which claims priority from Chinese Application Nos. 201710017182.7 filed Jan. 10, 2017 and 201720028892.5 filed Jan. 10, 2017, all of which are incorporated herein by reference.

FIELD OF THE INVENTION

The invention belongs to the technical field of industrial instruments and instrument testing and calibration, and particularly relates to an instrument calibration apparatus and a calibration method using the instrument calibration apparatus.

BACKGROUND OF THE INVENTION

To ensure the accuracy of instruments in actual applications at industrial sites, usually testing and calibration (abbreviated as "calibration") is required for the measured values or indicated values provided by the instruments. A basic method for testing and calibration is to directly compare the measured value or indicated value provided by the instrument with a standard value, so as to ascertain whether the measured value of the instrument is accurate, and then perform calibration as required.

Regarding instruments, there are mainly single-variable instruments and multi-variable meters in actual applications. A single-variable instrument means that the measured value of a single physical quantity is displayed directly on the instrument after the measured value of the physical quantity is connected to the instrument. However, there are often multiple varying physical quantities in a system, and all of them have influences on the system. In such a case, a multi-variable instrument has to be used for measurement.

For the calibration of such multi-variable instruments, two calibration methods, i.e., calibration by direct comparison and separate calibration of multiple variables, are both widely used presently.

The calibration by direct comparison is to simultaneously input multiple physical quantities to the tested instrument and a special calibration apparatus for calibration by comparison. After multiple physical quantities (pressure, temperature, electrical signal, and the like) are inputted to the tested instrument and the special calibration apparatus, the tested instrument and the special calibration apparatus use built-in calculation logics to process the physical quantities and provide final test results. For example, a flow calculator calculates flow information according to pressure (pressure difference), temperature, liquid density, and orifice diameter, and the like.

The traditional method of calibration by direct comparison can only use special-purpose calibration apparatuses in a field. For example, special-purpose flow calibration apparatuses have to be used in the flow field, special-purpose valve calibration apparatuses have to be used to test valve opening, and special-purpose methane concentration calibration apparatuses have to be used to test methane concentration. The user has to acquire and keep a special-purpose calibration apparatus for each type of equipment, which not only brings inconvenience to the user, but also causes increased cost to the user. In addition, multiple special-purpose calibration apparatuses are inconvenient to carry to a site together or can't be used in the field. Therefore, many instruments have to be calibrated in a laboratory.

The separate calibration of multiple variables is to simultaneously input multiple physical quantities to a tested instrument and a special calibration apparatus and then compare the inputted physical quantities between the tested instrument and the calibration apparatus for calibration. Since the tested instrument has to perform complex calculations of the inputted physical quantities to output final measurement results, it is unable to evaluate the overall error of the tested instrument by separate calibration of multiple variables (because different physical quantities have different weights in the calculations), though the error of each physical quantity can be evaluated by separate calibration of multiple variables; instead, an external computing system has to be used to evaluate the overall error of the tested instrument indirectly (manually). However, it is difficult for an external computing system to compute multiple variables accurately in real time, which introduces severe inconvenience to the calibration process.

CONTENTS OF THE INVENTION

To solve the above technical problems, the present invention provides an instrument calibration apparatus (or device) and a calibration method, which are convenient and easy to use, highly versatile, and applicable to real-time multi-variable measurement and calibration of instruments.

To attain the above objects, the present invention provides an instrument calibration apparatus, which comprises: a physical quantity input/output unit capable of inputting and outputting at least one first physical quantity; a physical quantity measurement unit configured to measure a value of said at least one first physical quantity inputted from the physical quantity input/output unit; a physical quantity configuration unit configured to generate a value of at least one second physical quantity from the value of said at least one first physical quantity through operations, or generate a value of at least one first physical quantity from a value of at least one second physical quantity through operations; a display unit configured to at least display a name and the value of the second physical quantity; a man-machine interaction unit configured to enable a user to manipulate the instrument calibration apparatus; a storage unit configured to store data required by the instrument calibration apparatus; and a control unit configured to perform control to execute a first mode in a case where the physical quantity to be measured is the second physical quantity and it is unnecessary for the instrument calibration apparatus to generate and output a standard value of said at least one first physical quantity to realize the measurement, or execute a second mode in a case where the physical quantity to be measured is the second physical quantity and it is necessary for the instrument calibration apparatus to generate and output a standard value of said at least one first physical quantity to realize the measurement, wherein, in the first mode, the physical quantity measurement unit is used to measure a value of at least one first physical quantity inputted from the physical quantity input/output unit and correlated with the second physical quantity, the physical quantity configuration unit is controlled to generate a value of the second physical quantity from the measured value of said at least one first physical quantity inputted, and the display unit is controlled to display a name and the generated value of the second physical quantity; and in the second mode, the physical quantity configuration unit is controlled to generate a standard value of the first physical quantity from a set standard value of at least one second physical quantity, and the physical quantity input/output unit is controlled to output the generated standard value of the first physical quantity, and the display unit is controlled to display a name of the second physical quantity and the set standard value.

The first physical quantity in the present invention refers to a physical quantity that can be detected or generated directly by the instrument, such as pressure, temperature, humidity, and voltage and current, and the like; the second physical quantity in the present invention refers to a physical quantity that can't be detected or generated directly by the instrument but has to be derived from the first physical quantity (e.g., conversion with a specified mathematical equation), such as (meteorological) altitude, daily air leakage volume, volumetric flow rate, methane concentration, and valve opening, and the like.

Furthermore, the present invention provides an instrument to be calibrated using the above-mentioned instrument calibration apparatus, which comprises: a physical quantity name designation step, in which the user designates the name of a physical quantity to be measured by the instrument to be calibrated; a mode designation or judgment step, in which the user designates an operating mode or the instrument calibration apparatus judges whether it is necessary to output a standard value of at least one first physical quantity to perform calibration; a first mode execution step, in which a first mode is executed in a case that the first mode is designated or it is judged that it is unnecessary to output a standard value of at least one first physical quantity; or a second mode execution step, in which a second mode is executed in a case that the second mode is designated or it is judged that it is necessary to output a standard value of at least one first physical quantity.

Another object of the present invention is to provide an instrument calibration apparatus suitable for real-time field calibration of multiple variables. The instrument calibration apparatus is provided with a handheld casing, and further comprising the following units that are electrically connected: a physical quantity input/output unit assembled on the casing and capable of inputting and outputting at least one first physical quantity, comprising at least one pressure interface, at least one current and voltage interface, a temperature interface, and a humidity interface, which are independent from each other respectively; a physical quantity measurement unit assembled inside the casing and configured to measure a value of said at least one first physical quantity inputted from the physical quantity input/output unit, comprising at least one pressure module, at least one current and voltage module, a temperature module, and a humidity module, which are electrically connected to the interfaces in the physical quantity input/output unit respectively; a physical quantity configuration unit configured to generate a value of at least one second physical quantity from the value of said at least one first physical quantity through operations, or generate a value of at least one first physical quantity from a value of at least one second physical quantity through operations; a display unit assembled on the casing and configured to at least display a name and the value of the second physical quantity; a man-machine interaction unit, in the form of a touchpad disposed on the display unit and configured to manipulate the instrument calibration apparatus; a storage unit configured to store data required by the instrument calibration apparatus; and a control unit configured to control the physical quantity input/output unit, the physical quantity measurement unit, the physical quantity configuration unit, and the display unit.

In the above-mentioned instrument calibration apparatus for real-time field multi-variable measurement and calibration, the pressure input/output interface is a gas pipeline interface. The current and voltage input/output interface is a terminal block or a plug and socket connector for electrical connection. The first physical quantity refers to a physical quantity that can be detected or generated directly by the instrument, including pressure, temperature, humidity, and voltage and current; the second physical quantity refers to meteorological altitude, daily air leakage volume, volumetric flow rate, methane concentration, or valve opening.

Particularly, in the instrument calibration apparatus, the first physical quantity is pressure, and the physical quantity measurement unit is a pressure measurement module for measuring pressure. In that mode, the apparatus further comprises a standard pressure supply unit configured to supply standard pressure, which connects to the display unit to display the standard pressure and supplies the standard pressure to the exterior.

With the above design, the present invention attains the following beneficial technical effects:

A. A variety of measurement modules, a physical quantity configuration unit capable of performing physical quantity conversion, and physical quantity input/output units for pressure and current, and the like, are integrated in the instrument calibration apparatus in the present invention, and the instrument calibration apparatus can present the final values of the physical quantities intuitively. Thus, it is unnecessary to perform cumbersome manual conversions at each calibration point in the measurement and calibration of a multi-variable instrument, and the instrument calibration apparatus is convenient, easy to use, and highly efficient.

B. A variety of interfaces and a plurality of unit modules are integrated inside the handheld casing in the present invention. Thus, the apparatus is versatile, easy to carry and convenient to use, and suitable for use in the field.

C. The instrument calibration apparatus in the present invention can perform measurement and calibration of a variety of instruments or multi-variable instruments with a universal instrument. Thus, the instrument calibration apparatus has high versatility, and attains technical effects of expanding the application domain of the universal instrument and reducing the calibration cost.

D. The instrument calibration apparatus in the present invention can perform real-time measurement and calibration of multi-variable instruments, and attains technical effects of real-time calculation, real-time adjustment, and real-time calibration.

E. The instrument calibration apparatus in the present invention is provided with a communication unit and thereby has a built-in remote communication function, which eliminates any intermediate communication medium and enables intelligent interaction with a remote database through a network.

DESCRIPTION OF REFERENCE NUMBERS

100—instrument calibration apparatus;
10—physical quantity input/output unit; 11—pressure output interface; 12—humidity interface; 13—temperature interface; 14—current and voltage interface; 15—standard pressure interface;
20—physical quantity measurement unit; 21—pressure module; 22—humidity module; 23—temperature module; 24—current and voltage module; 25—standard pressure module;
30—physical quantity configuration unit; 40—display unit; 50—communication unit; 60—control unit; 70—man-machine interaction unit; 80—storage unit;
90—image capturing unit; 91—camera

DETAILED DESCRIPTION OF THE EMBODIMENTS

Hereunder the instrument calibration apparatus and the calibration method will be detailed in embodiments with reference to the accompanying drawings. In addition, it should be noted that the instrument calibration apparatus and the calibration method are not limited to the following embodiments, but may be implemented with different variations. In all embodiments, the same structural elements are designated with the same symbols. In addition, the dimensional scales of the accompanying drawings are used only for the convenience of description and may be different from the actual ones; moreover, sometimes parts of the structures may be omitted in the accompanying drawings.

Figure 1A:
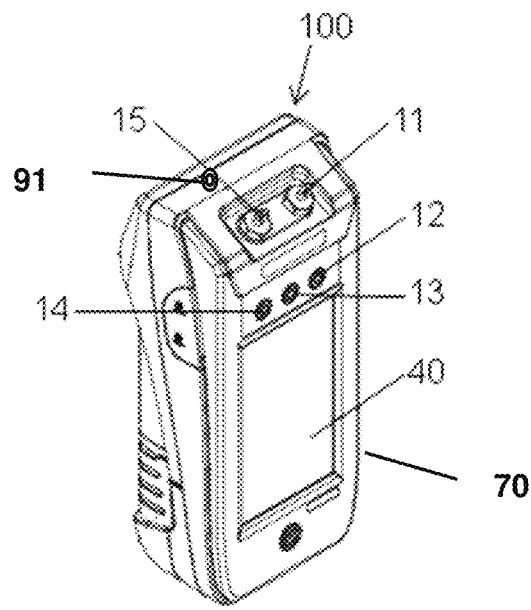
FIG. 1A is an external structural diagram of the instrument calibration apparatus in the present invention.
Figure 1B:
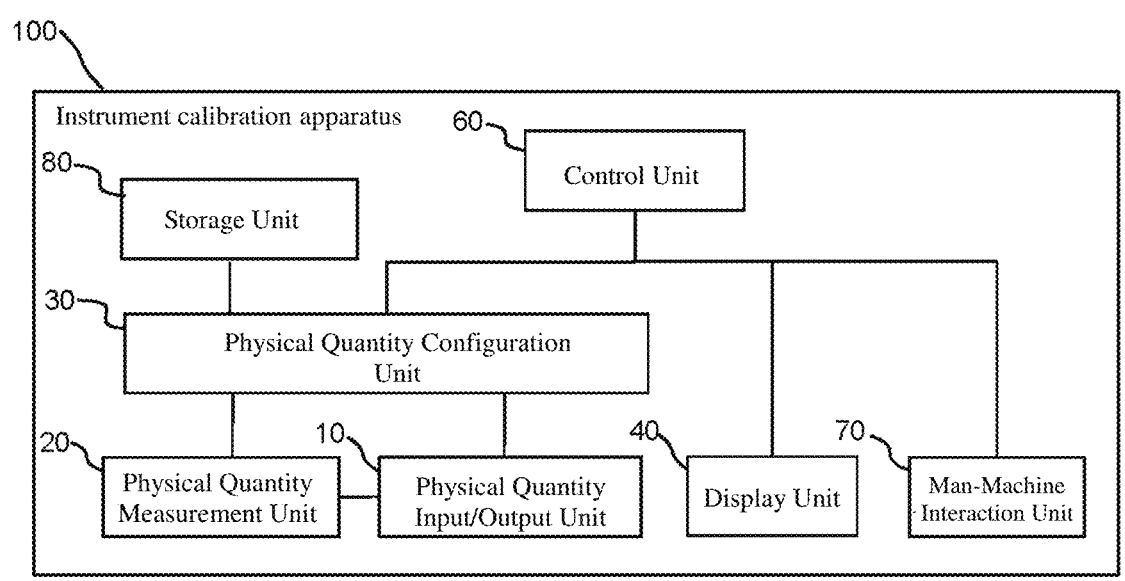
FIG. 1B is an overall structural block diagram of the calibration apparatus in an embodiment of the present invention.

Please see FIG. 1B, the instrument calibration apparatus 100 in an embodiment of the present invention comprises: a physical quantity input/output unit 10, a physical quantity measurement unit 20, a physical quantity configuration unit 30, a display unit 40, a control unit 60, a man-machine interaction unit 70, and a storage unit 80.

The physical quantity input/output unit 10 is capable of inputting and outputting at least one first physical quantity. Here, the first physical quantity refers to a physical quantity that can be detected or generated directly by the instrument, such as pressure, temperature, humidity, and voltage and current, and the like. The second physical quantity refers to a physical quantity that can't be detected or generated directly by the instrument but has to be derived from the first physical quantity (e.g., conversion with a specified mathematical equation), such as (meteorological) altitude, daily air leakage volume, volumetric flow rate, methane concentration, and valve opening, and the like.

Figure 1C:
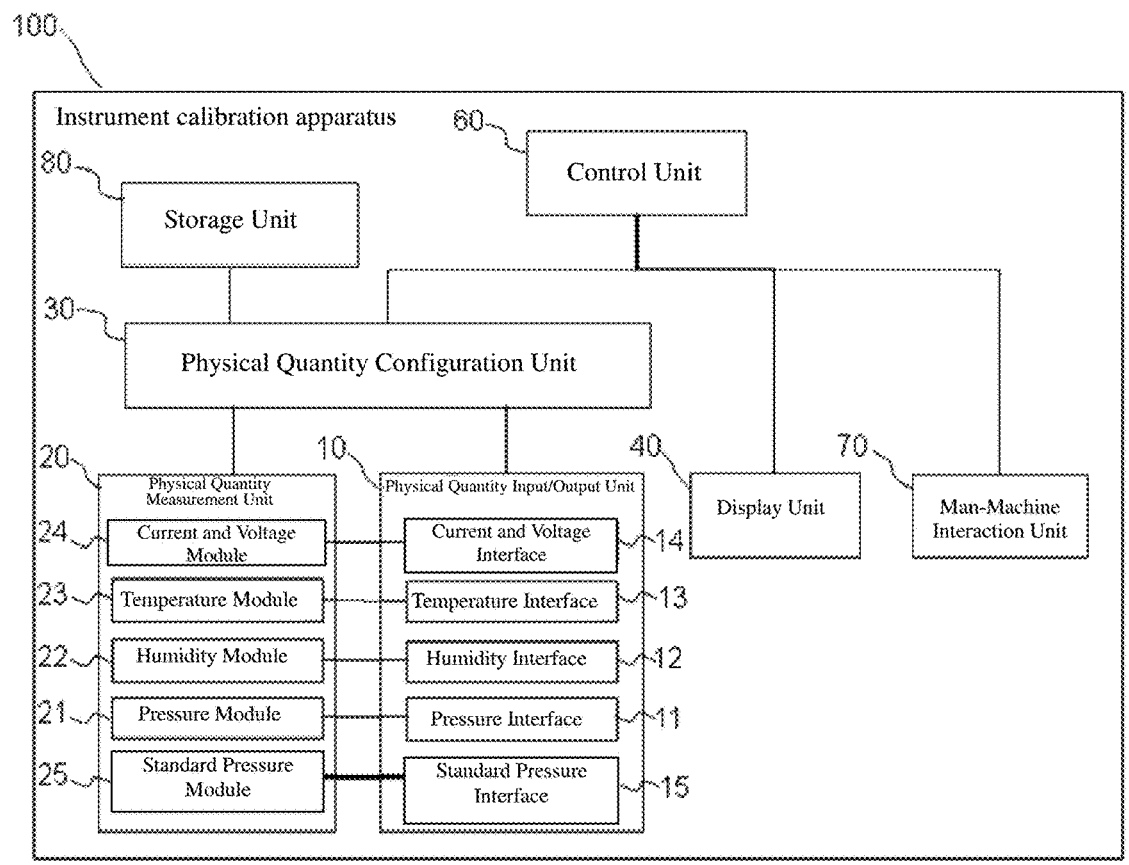
FIG. 1C is an overall structural block diagram of the calibration apparatus in another embodiment of the present invention.

Please see FIGS. 1A and 1C. The instrument calibration apparatus 100 comprises a handheld casing. The physical quantity input/output unit 10 is assembled on the casing, and, for example, may comprise at least one pressure output interface 11 (e.g., a gas pipeline interface) for pressure output (connected to the tested instrument), at least one voltage and current interface 14 (e.g., a terminal block or plug and socket connector for electrical connection) for input/output of current or voltage, a temperature interface 13 for mounting a temperature sensor, and a humidity interface 14 for mounting a humidity sensor, and the like, which are independent from each other respectively; the apparatus further comprises a standard pressure interface 15 for mounting a standard pressure gauge during pressure calibration.

The physical quantity measurement unit 20 measures the value of at least one first physical quantity inputted from the physical quantity input unit 10. The physical quantity measurement unit 20 may be assembled inside the casing, and, for example, may comprise a pressure module 21 for measuring pressure and a standard pressure module 25 for supplying standard pressure, a voltage and current module 24 for measuring voltage and current, a temperature module 23 for measuring temperature, and a humidity module 22 for measuring humidity, and the like. The pressure module 21 is in signal connection with the pressure interface 11, the standard pressure module 25 is in gas connection with the standard pressure interface 15 and electrically connected to the display unit 40, the voltage and current module 24 is in signal connection with the voltage and current interface 14, the temperature module 23 is in signal connection with the temperature interface 13, and the humidity module 22 is in signal connection with the humidity measurement interface 12.

The physical quantity configuration unit 30 may be assembled in the casing, and generates a value of at least one second physical quantity from a value of at least one first physical quantity through operations, or generates a standard value of at least one first physical quantity from a value of at least one second physical quantity through operations.

The first physical quantity and the second physical quantity usually have a functional relation with each other. For example, air pressure and meteorological altitude has a functional relation with each other as represented by the equation 1, which is referred to as a conversion equation.

$$P = (H \cdot T_0^L | 1) - g_0/L \cdot R \cdot p_0 \qquad \text{(equation 1)}$$

Where,
H: geopotential height of a place above (or below) mean sea level (m);
P: atmospheric pressure at the place H (hPa);
$p_0$: normal atmospheric pressure at mean sea level (1013.25 hPa);
$T_0$: atmospheric thermodynamic temperature at mean sea level (288.15K);
L: vertical Gradient of atmospheric temperature in troposphere (−0.0065K/m);
$g_0$: normal acceleration of gravity (9.80665 m/s$^2$);
R: specific air constant of dry air (287.05287 J/K*kg);

In the above equation 1, P is atmospheric pressure and is a first physical quantity, and H is meteorological altitude and is a second physical quantity. Besides a first physical quantity and a second physical quantity, the conversion equation further includes other physical quantities (e.g., atmospheric thermodynamic temperature) and constants (e.g., gravitational acceleration). Owing to the fact that the atmospheric thermodynamic temperature at mean sea level is a stable physical quantity, it appears as a fixed value in the conversion equation, similar to the constants such as gravitational acceleration, and the like. Those values are referred to as environmental parameters.

With the conversion equation based on a functional relation, the meteorological altitude that is the second physical quantity can be generated from the measured atmospheric pressure that is the first physical quantity. The physical quantity configuration unit 30 performs the above-mentioned operations to convert at least one first physical quantity to at least one second physical quantity or convert at least one second physical quantity to at least one first physical quantity, for example, based on an equation that represents the relation between the first physical quantity and the second physical quantity.

Here, the conversion equation between the first physical quantity and the second physical quantity may be directly inputted (written) externally by the user, for example, via the man-machine interaction unit 70 described below, or may be pre-stored in the storage unit 80 described below. Of course, the relation between the first physical quantity and the second physical quantity is not limited to the functional relation illustrated above, and may be a different relation, such as a numerical table. Such numerical tables may be pre-stored in the storage unit 80. Based on the user's instruction, under the control of the control unit 60, the physical quantity configuration unit 30 can select a corresponding equation to perform operations or use a numerical table to convert the first physical quantity to the second physical quantity or convert the second physical quantity to the first physical quantity.

Under the control of the control unit 60, the display unit 40 at least can display the name and value of the second physical quantity, as well as the name and value of the first physical quantity, and the like. The display unit 40 is assembled on the casing, and may be a general-purpose display screen, such as a liquid crystal display (LCD) or organic EL (Electro-Luminescence) display (OLED), and the like. An essential feature of the present invention is that the instrument calibration apparatus 100 comprises a physical quantity configuration unit 30. Therefore, in a preferred embodiment of the present invention, the display unit 40 can display the equation that represents the relation between the first physical quantity and the second physical quantity, and can work with the man-machine interaction unit 70 to support equation inputting and editing.

The control unit 60 issues commands to the physical quantity configuration unit 30, the physical quantity measurement unit 20, and the physical quantity input/output unit 10, and the like, and controls them. The control unit 60 may comprise a microprocessor, a digital signal processor, or other hardware processors.

The man-machine interaction unit 70 is used to enable the user to manipulate the instrument calibration apparatus 100, for example, indicating the physical quantity to be measured, and instructing to start the measurement, and the like. An essential feature of the present invention is that the instrument calibration apparatus 100 comprises a physical quantity configuration unit 30. Therefore, in a preferred embodiment of the present invention, the man-machine interaction unit 70 comprises an equation editor interface where the conversion equation between the first physical quantity and the second physical quantity can be inputted and edited. The user may create or edit a corresponding conversion equation, or select an equation that has been stored or edited previously, via the equation editor interface. The man-machine interaction unit 70 may be a touchpad disposed on the display unit 40. In that case, the user can input (write) and edit an equation via the equation editor interface shown in FIG. 2, for example.

The storage unit 80 at least can store conversion equations between a first physical quantity and a second physical quantity that are inputted or edited via the man-machine interaction unit 70. Of course, the storage unit 80 can also store conversion equations between a first physical quantity and a second physical quantity in advance, as well as common coefficients, such as circumference ratio and gravitational acceleration, and the like. Furthermore, the storage unit 80 can store the operating status of the tested instrument and environmental parameters, and the like.

The storage unit 80 may be any known volatile memory and/or nonvolatile memory for storing data and/or instructions. For example, the storage unit 80 may comprise read-only memory (ROM), random access memory (RAM), flash memory, magnetic storage media, CD-ROM, erasable and programmable read-only memory (EPROM), and programmable read-only memory (PROM), and the like. The storage unit 80 may be a permanent storage unit or removable storage unit, or a combination thereof.

Figure 1D:
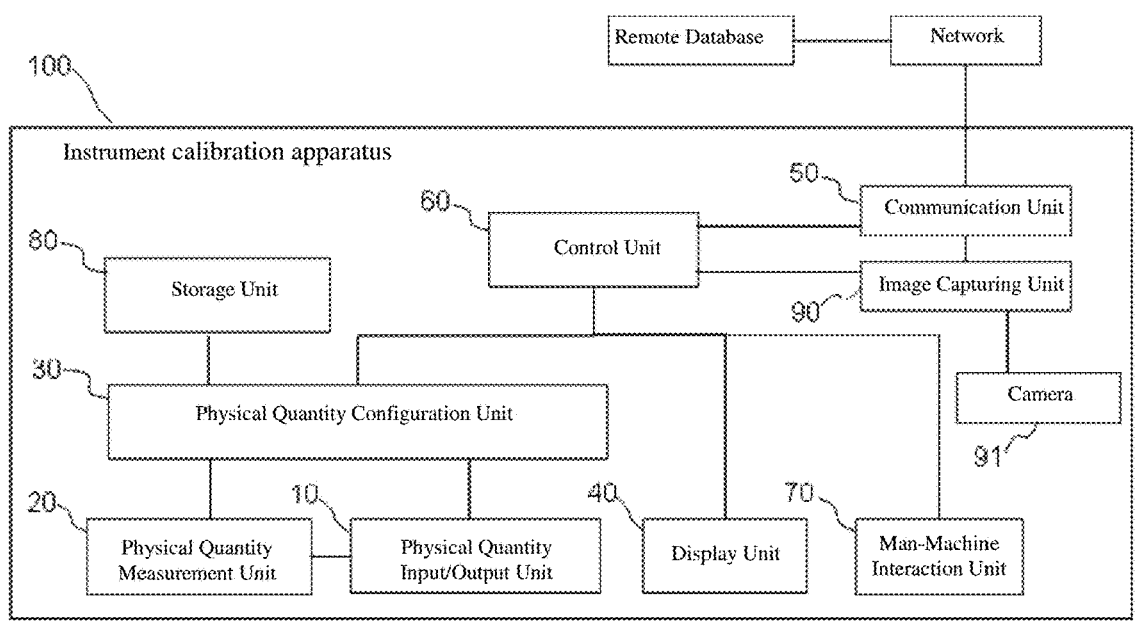
FIG. 1D is an overall structural block diagram of the calibration apparatus in an extended embodiment of the present invention.

An instrument calibration apparatus may be extended on the basis of the configurations shown in FIGS. 1B and 1C. An extended embodiment that is extended on the basis of the configuration in FIG. 1B is shown in FIG. 1D (similarly, the instrument calibration apparatus may be extended on the basis of the configuration shown in FIG. 1C). The control unit 60 is further connected with a communication unit 50, which can communicate with a remote database through a network. The communication unit 50 accomplishes data interaction between the system and the remote database, and has a remote communication function. In terms of the implementation form, the communication unit 50 may be a communication program integrated in the control unit 60, and, in that case, the control unit is provided with a network interface to access the network; alternatively, the communication unit may be a separate hardware module, for example, the communication unit 50 has a connecting plug and a network interface, wherein the connecting plug is configured to couple to the control unit to realize a mechanical connection and an electrical connection between the communication unit 50 and the control unit 60, the network interface is communicated with the network and accesses the database through the network, wherein the network may be an Internet-based industrial Ethernet or a wireless network that supports Internet connection to realize the remote communication function.

In this extended embodiment of the instrument calibration apparatus, a communication unit 50 is integrated inside the instrument calibration apparatus, so that the instrument calibration apparatus is imparted with a built-in remote communication function, and any intermediate communication medium is omitted. As long as the instrument calibration apparatus is connected to a supported network, it can be connected to a remote database after simple setting. Thus, the instrument calibration apparatus can download pre-stored basic information of the tested instrument (e.g., scale, accuracy, ID, and manufacturer information, and the like, of a tested pressure instrument) from the database in real time, historical calibration data of the tested instrument (including variable categories, indicated values at all calibration points, and indication errors, and the like), and a calibration scheme (including an automatic calibration procedure for calibration operations), and thereby the calibration data of the variables of the tested instrument can be generated automatically, and the calibration data can be uploaded through the network to the remote database in real time.

Another instrument calibration apparatus may be further extended, as shown in the example in FIG. 1D: the control unit 60 may be further connected with an image capturing unit 90, which is connected to a camera 91 assembled on the casing, with an image recognition program embedded in the image capturing unit 90. The camera 91 faces the front side of the tested instrument and can capture an image of the data and model information on the dial of the tested instrument and the appearance characteristics of the tested instrument, the image is recognized by the image recognition program in the image capturing unit 90, and thereby the model and basic information of the tested instrument can be obtained, such as scale, accuracy, ID and manufacturer information, and the like, of the instrument, and then the information can be transmitted via the communication unit 50 to the remote database under the control of the control unit 60.

The control unit 60 performs control so that a first mode is executed in a case where the physical quantity to be measured is the second physical quantity and it is unnecessary for the instrument calibration apparatus 100 to generate and output a standard value of at least one first physical quantity to realize the measurement, or a second mode is executed in a case where the physical quantity to be measured is the second physical quantity and it is necessary for the instrument calibration apparatus 100 to generate and output a standard value of at least one first physical quantity to realize the measurement.

Whether it is necessary to output a standard value of at least one first physical quantity or not may be specified by the user via the man-machine interaction unit, or may be judged by the control unit 60, for example, according to the name of the second physical quantity designated by the user or the operating status of the physical quantity input/output unit 10 (e.g., there is no input of any first physical quantity in the instrument calibration apparatus 100); in the case that the control unit 60 judges it is necessary to output a standard value of at least one first physical quantity to realize measurement, the standard value of at least one first physical quantity may be obtained by operation with an inverse function from a standard value of the second physical quantity set by the user.

In the first mode, the physical quantity measurement unit 20 is controlled to measure the value of at least one first physical quantity inputted from the physical quantity input/output unit 10 and correlated with the second physical quantity; the physical quantity configuration unit 30 is controlled to generate a standard value of the second physical quantity from the measured value of at least one inputted first physical quantity; and the display unit 40 is controlled to display the generated name and standard value of the second physical quantity.

In the second mode, the physical quantity configuration unit 30 is controlled to generate and output a standard value of the first physical quantity from a set standard value of at least one second physical quantity, and the display unit 40 displays the name of the second physical quantity and the set standard value. Here, the set standard value of at least one second physical quantity may be set appropriately by the user according to the measured value of the measured physical quantity (i.e., indicated value on the instrument to be calibrated), or may be set automatically by the instrument calibration apparatus 100.

While in a case that the measured physical quantity is the second physical quantity, the above first mode and second mode may also be executed in a case that the measured physical quantity is the first physical quantity. In the latter case, the conversion between the first physical quantity and the second physical quantity can be omitted. That is obvious.

Figure 2:
FIG. 2 is a schematic diagram illustrating an example of the equation editor interface in the man-machine interaction unit 70 in an embodiment of the present invention.

Now an example of the equation editor interface of the man-machine interaction unit 60 will be described with reference to FIG. 2. The equation editor interface provides functions for creating, editing, selecting, and deleting an equation. During equation editing, corresponding physical quantities, environmental parameters and coefficients, and operation symbols corresponding a combination of linear, non-linear, and other operations (e.g., "exp" and "log", and the like. shown in FIG. 2) can be selected for editing.

Hereunder the calibration method for calibrating an instrument with the instrument calibration apparatus 100 in this embodiment will be described in an example where the physical quantity to be measured by the instrument to be calibrated (i.e. tested instrument) is the second physical quantity with reference to FIGS. 3-5. The calibration method comprises calibration in measurement mode and calibration in output mode. Calibration in measurement mode is performed in a case where the physical quantity to be measured by the tested instrument is the second physical quantity and it is unnecessary to generate and output a standard value of at least one first physical quantity. Calibration in output mode is performed in a case where the physical quantity to be measured by the tested instrument is the second physical quantity and it is necessary to generate and output a standard value of at least one first physical quantity. While the invention is described here in an example where the tested instrument is a multi-variable instrument, alternatively the tested instrument may be a single-variable instrument. Besides, the instrument calibration apparatus 100 should be connected appropriately with the tested instrument when the tested instrument is to be calibrated with the instrument calibration apparatus 100. Since such a connection belongs to prior art, it is not detailed here.

Figure 3:
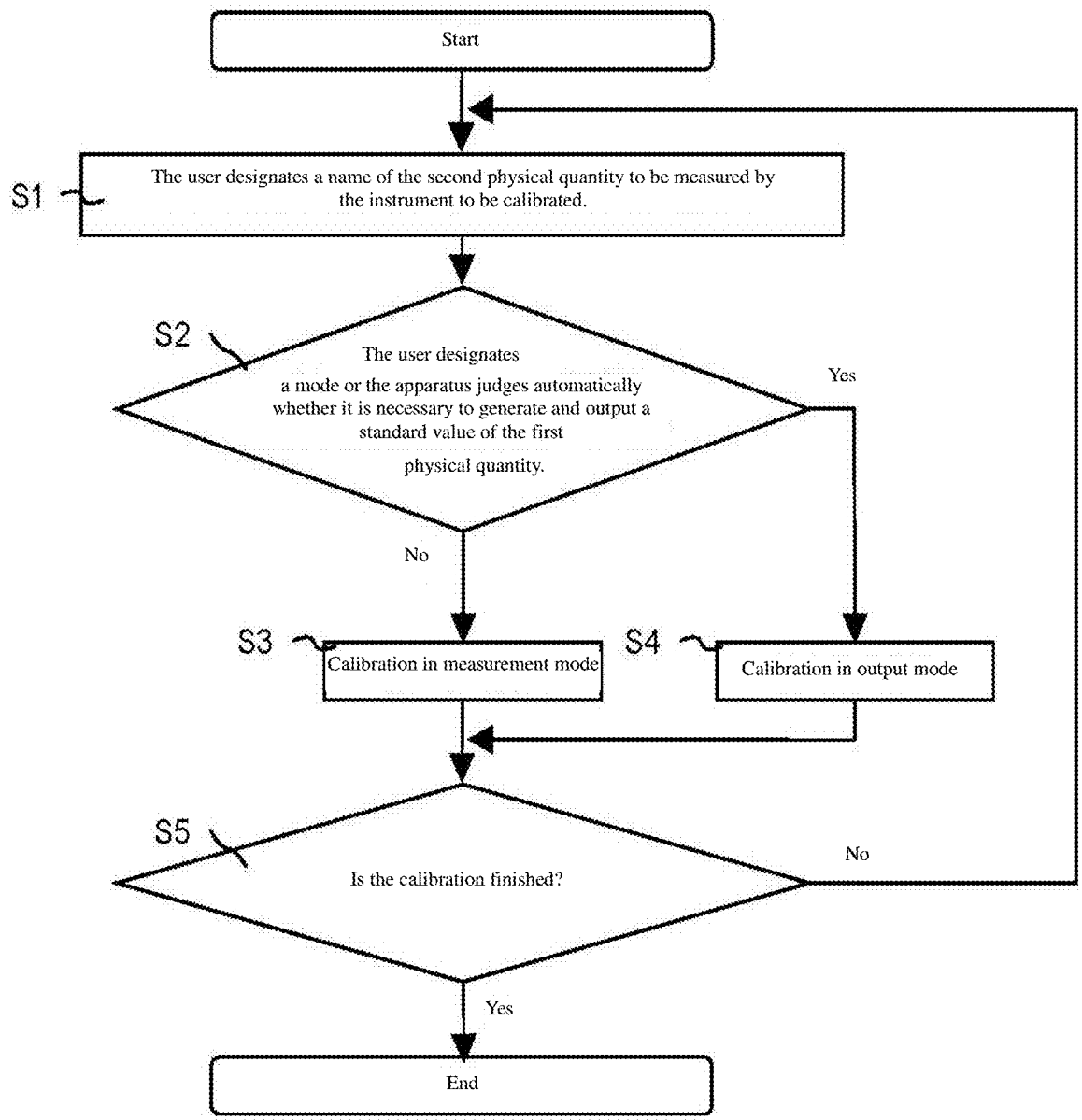
FIG. 3 is an overall flow diagram of the calibration method in an embodiment of the present invention.

FIG. 3 is an overall flow diagram of the calibration method. First, in step S1, the user designates the name of a second physical quantity to be measured by the tested instrument. Next, in step S2, the user designates the operating mode of the instrument calibration apparatus 100 or the instrument calibration apparatus 100 automatically judges whether it is necessary to generate and output a standard value of at least one first physical quantity, for example, according to the name of the second physical quantity. In a case that the measurement mode is designated or it is judged that it is unnecessary to output a standard value of at least one first physical quantity, the procedure proceeds to step S3, where calibration in measurement mode is performed under the control of the control unit 60. In a case that the output mode is designated or it is judged that it is necessary to output a standard value of at least one first physical quantity in the step S2, the procedure skips to step S4, where calibration in output mode is performed under the control of the control unit 60. After either calibration in measurement mode or calibration in output mode is completed, the user instructs whether to terminate the calibration in step S5. The calibration is terminated if the user instructs to terminate the calibration, or the procedure returns to the step S1 and waits for a next instruction from the user if further calibration is required.

While it is described that the user designates the name of a second physical quantity to be measured by the tested instrument firstly and then designates the operating mode of the instrument calibration apparatus 100 or the instrument calibration apparatus 100 automatically judges whether it is necessary to generate and output a standard value of at least one first physical quantity in the overall flow shown in FIG. 3, the present invention is not limited to the above embodiment. Alternatively, the user may designate calibration in measurement mode or calibration in output mode firstly, and then designate the name of a second physical quantity to be measured by the tested instrument. In that case, alternatively the user may designate the name of a second physical quantity to be measured by the tested instrument after the instrument calibration apparatus is set to perform calibration in measurement mode or calibration in output mode.

Figure 4:
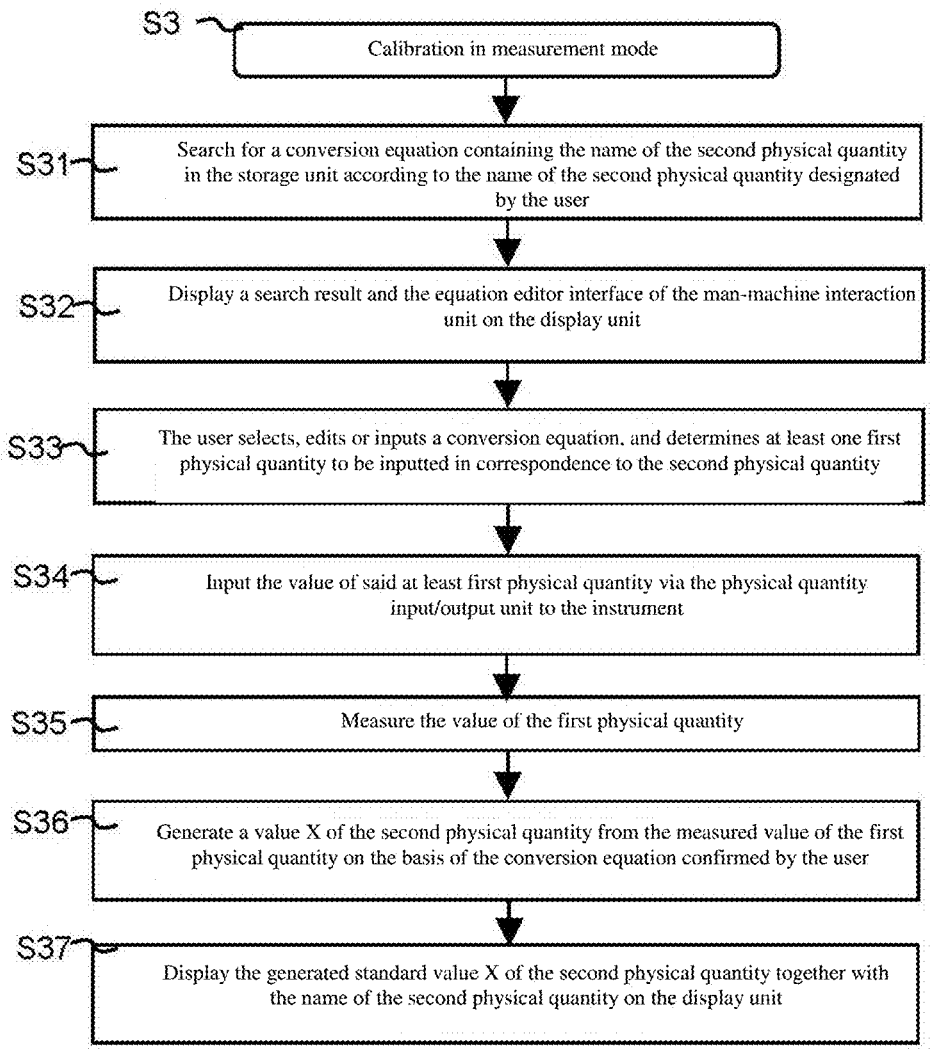
FIG. 4 is a flow diagram of calibration in measurement mode in the calibration method in an embodiment of the present invention.

FIG. 4 is a flow diagram of the method of calibration in measurement mode (i.e., the sub-steps in the step S3 in FIG. 3). As shown in FIG. 4, first, in step S31, a conversion equation containing the name of the second physical quantity is searched for in the storage unit 80 according to the name of the second physical quantity designated by the user in the step S1, then, in step S32, a search result and the equation editor interface of the man-machine interaction unit 70 are displayed on the display unit 40. Here, if at least one conversion equation is stored in the storage unit, all of the conversion equations will be displayed in the equation editor interface for the user to select and edit. If no conversion equation is found in the search, the equation editor interface will be displayed to prompt the user to input (write) a conversion equation. In step S33, the user selects, edits, or inputs (writes) a conversion equation via the equation editor interface, determines at least one first physical quantity in correspondence to the second physical quantity, and then provides a confirmation indication. After the user confirms the conversion equation to be used and said at least one first physical quantity, in step S34, the said at least one first physical quantity is inputted via the physical quantity input/output unit 10 to the instrument calibration apparatus 100.

In step S35, the physical quantity measurement unit 20 is controlled to measure the value of said at least one first physical quantity inputted from the physical quantity input/output unit 10 and correlated with the second physical quantity, and the measured value of said at least one first physical quantity is inputted to the physical quantity configuration unit 30.

In step S36, the physical quantity configuration unit 30 generates the value X of a second physical quantity from the measured value of the first physical quantity on the basis of the conversion equation determined in the step S33.

In step S37, the generated value X of the second physical quantity (as a standard value of the second physical quantity for calibration) is displayed together with the name of the second physical quantity on the display unit 40. The user compares the generated value X with the measured value $R_0$ of the second physical quantity measured by the tested instrument, to obtain a difference between the two values. The tested instrument is calibrated according to the result of comparison.

In the above calibration in measurement mode, actual physical quantities (pressure, temperature, and electrical signal, and the like) are inputted to the instrument calibration apparatus 100 that serve as a calibration apparatus, a corresponding conversion equation is selected from multi-variable conversion equations (e.g., a functional relation created via the equation editor interface), the physical quantity configuration unit calculates a standard value of the physical quantity measured by the tested instrument in real time according to the changed value of the inputted physical quantity, and the standard value is displayed in real time. Thus, the indicated value from the tested instrument in real time is compared with a standard value of the calibration apparatus, and thereby calibration in measurement mode is realized.

Compared with traditional calibration methods, the calibration method provided above can present the final value of the physical quantity intuitively, it is unnecessary to perform cumbersome manual conversions at each calibration point. The calibration method above is convenient, easy to use, and highly efficient.

In addition, the measuring and calibrating to a variety of multi-variable instruments can be performed with a universal instrument calibration apparatus. Thus, the instrument calibration apparatus has high versatility, and attains technical effects of expanding the application domain of the universal instrument and reducing the calibration cost.

Figure 5:
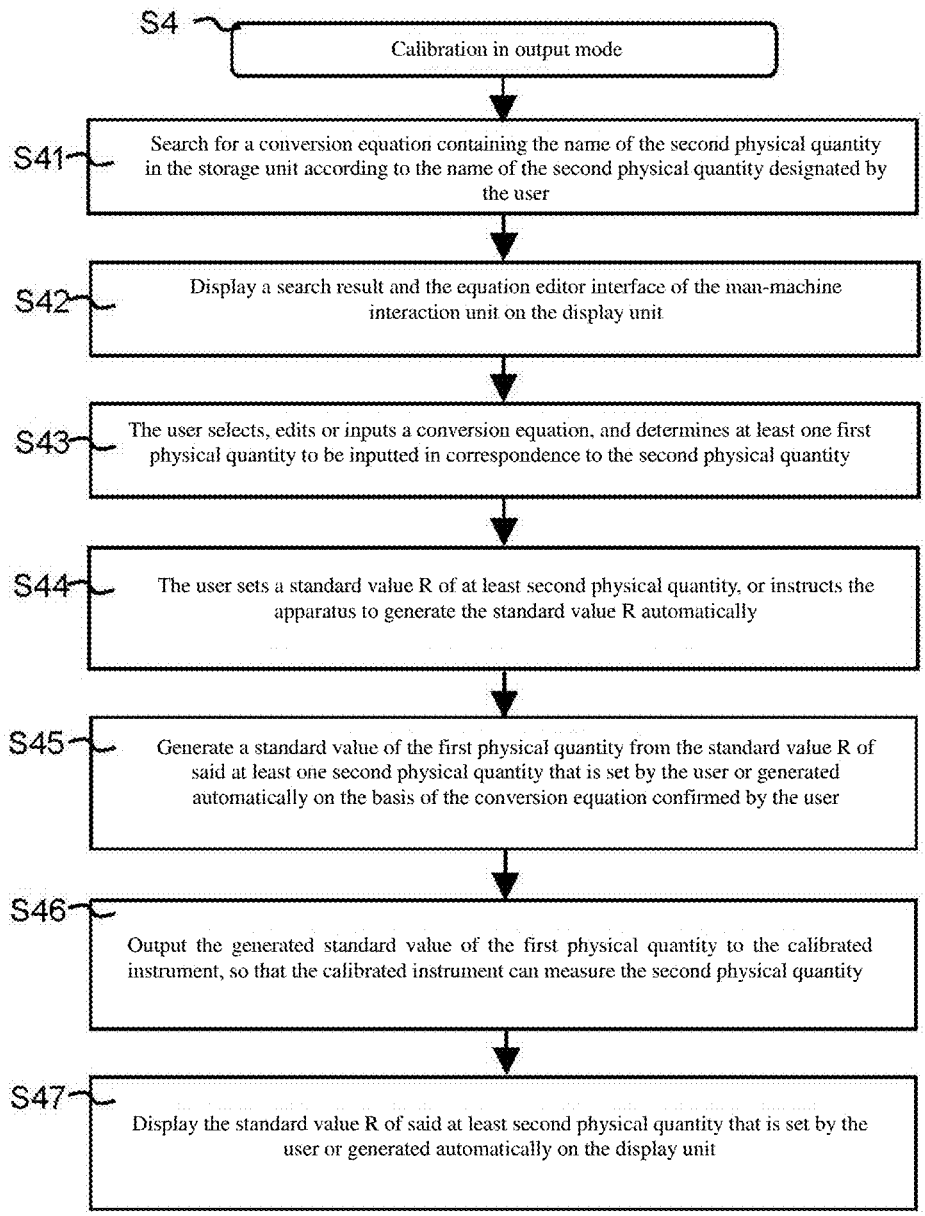
FIG. 5 is a schematic diagram of calibration in output mode in the calibration method in an embodiment of the present invention.

FIG. 5 is a schematic diagram illustrating the method of calibration in output mode (i.e., the sub-steps in the step S4 in FIG. 3). As shown in FIG. 5, first, in step S41, a conversion equation containing the name of the second physical quantity is searched for in the storage unit 80 according to the name of the second physical quantity designated by the user in the step S1, then, in step S42, a search result and the equation editor interface of the man-machine interaction unit 70 are displayed on the display unit 40. Here, if at least one conversion equation is stored in the storage unit, all of the conversion equations will be displayed in the equation editor interface for the user to select and edit. If no conversion equation is found in the search, the equation editor interface will be displayed to prompt the user to input (write) a conversion equation. In step S43, the user selects, edits, or inputs (writes) a conversion equation via the equation editor interface, determines at least one first physical quantity to be inputted in correspondence to the second physical quantity, and then provides a confirmation indication. In step S44, the user sets a standard value R of said at least one second physical quantity according to the range of the measured value of the second physical quantity to be measured by the tested instrument, or instructs the instrument calibration apparatus 100 to set a standard value R automatically.

In step S45, the control unit 60 controls the physical quantity configuration unit 30 to generate a standard value of the first physical quantity from the standard value R of said at least one second physical quantity set by the user or the standard value R of said at least one second physical quantity set automatically by the instrument calibration apparatus 100 in the step S44, on the basis of the conversion equation confirmed in the step S43.

In step S46, the generated standard value of the first physical quantity is outputted to the tested instrument, so that the tested instrument can measure the second physical quantity. Next, in step S47, the standard value R of at least one at least one second physical quantity set by the user or generated automatically by the instrument calibration apparatus 100 is displayed on the display unit 40, and the user compares a measured value $R_0$ of the second physical quantity measured by the tested instrument on the basis of the standard value of the first physical quantity with the set standard value R of the second physical quantity, to obtain the difference between the two values. The tested instrument is calibrated according to the result of comparison.

In the above calibration in output mode, for a second physical quantity to be measured by the tested instrument, a corresponding conversion equation is selected form multi-variable conversion equations (e.g., a functional relation created by editing on the basis of an inverse function), a first physical quantity is outputted (supplied) on the standard value from the instrument calibration apparatus 100 that serves as a calibration apparatus to the input side of the tested instrument, and the real-time tested (indicated) value of the tested instrument is compared with a nominal value (set value) according to the change of the supplied standard value. Thus, real-time measurement and calibration of a multi-variable instrument (calibration in output mode) is realized (e.g., according to the change of the standard pressure supplied from the instrument calibration apparatus 100 that serves as a calibration apparatus, the real-time indicated value of the tested instrument is compared with the standard value from the calibration apparatus, and thereby real-time measurement and calibration in output mode is realized).

Based on the method of calibration in measurement mode in conjunction with calibration in output mode, a multi-variable standard calibration apparatus is realized, and the apparatus not only can perform multi-variable standard measurement, but also can provide a multi-variable standard output. Through the multi-variable standard measurement, standard measurement values of multiple variables are obtained; through adjustment and control of the multi-variable standard output, standard output values of multiple variables are obtained.

In calibration in output mode, the multi-variable standard output can be adjusted in real time, and real-time calculation and calibration can be performed. Thus, compared with the prior art, the calibration method provided above attains effects of real-time calculation, real-time adjustment, and real-time calibration.

Similar to the above method of calibration in measurement mode, compared with traditional calibration methods, the method of calibration in output mode can present the final value of the physical quantity intuitively, it is unnecessary to perform cumbersome manual conversions at each calibration point, and the method is convenient, easy to use, and highly efficient.

In addition, the measurement and calibration of a variety of instruments or multi-variable instruments can be performed with a universal instrument calibration apparatus. Thus, the instrument calibration apparatus has high versatility, and attains technical effects of expanding the application domain of the universal instrument calibration apparatus and reducing the calibration cost.

In the configuration of multiple physical quantities in the instrument calibration apparatus 100, pressure may be selected as a main variable. In that case, the first physical quantity comprises pressure, and the physical quantity measurement unit 20 comprises a pressure module 21 for measuring pressure. The instrument calibration apparatus 100 further comprises a standard pressure module 25 for supplying standard pressure, which is in a gas connection with the standard pressure interface 15 of the physical quantity input/output unit 10 (see FIG. 1C), and is electrically connected to the display unit 40, so as to display the supplied standard pressure and supply the standard pressure via the standard pressure interface 15 to the exterior. The standard pressure module 25 may comprise a pressure controller, a pressure generator, and a pressure pipeline. In calibration in output mode, the pressure controller controls the pressure generated by the pressure generator to match the standard value of the first physical quantity (target pressure value) generated by the physical quantity configuration unit 30 on the basis of the set pressure value, according to the pressure in the pressure pipeline measured by the pressure measurement module, and supplies the pressure via the pressure pipeline to an external testing instrument/system. The pressure generator may be disposed inside the instrument calibration apparatus 100 or outside the instrument calibration apparatus 100.

Furthermore, besides the temperature module 23, the humidity module 22, the current and voltage module 24 (see FIG. 1C), the physical quantity measurement unit 20 may be further equipped with an ON/OFF measurement module and a current output module. The pressure module 21 and those modules all may be external modules of the system, which may be connected to the system through plug-in wires. At least two plug-in interfaces (A/B) are provided in the system, and each of the interfaces may be freely connected to an external pressure or temperature measurement module. Thus, different operating modes with two pressure measurement connections, two temperature measurement connections, or one pressure measurement connection and one temperature measurement connection can be provided according to the specific requirement for the system; in the system, it is advantageous to provide multiple plug-in interfaces (A/B), each of which can be freely connected to a measurement module for a variable to be measured, so that pressure measurement mode, temperature measurement mode, humidity measurement mode, current or voltage measurement mode, and the like, can be provided according to the specific requirement for the system.

Hereunder some embodiments of the present invention will be detailed.

Embodiment 1: Example of Calibration Application for a Differential Pressure Flowmeter (Calibration in Measurement Mode)

A differential pressure flowmeter is designed under a throttling principle based on Bernoulli equation and fluid continuity equation. Specifically, as a fluid flows through a throttling element (e.g., standard orifice plate, standard nozzle, long-radius nozzle, classic Venturi mouthpiece, or Venturi nozzle, and the like), a pressure difference is generated across the throttling element, and the value of the differential pressure is proportional to the square of the flow rate of the liquid. Among differential pressure flowmeters, standard orifice throttling differential pressure flowmeters are applied the most widely, because they have a simple structure and low manufacturing cost, are studied and analyzed the most comprehensively, and have been standardized. Hereinafter an application of the instrument calibration apparatus 100 to calibration of an orifice flowmeter will be described.

The relation between the volumetric flow rate $Q_f$ through an orifice plate and the differential pressure $\Delta p$ across the orifice plate meets the following equation 2.

$$Q_f = \frac{c}{\sqrt{1-\beta^4}} \cdot \epsilon \cdot \frac{\pi}{4} \cdot d^2 \cdot \sqrt{\frac{2\Delta P}{\rho_1}} \qquad \text{(equation 2)}$$

$Q_f$: volumetric flow rate under operating conditions, m³/s;
c: efflux coefficient, dimensionless;
β: d/D, dimensionless;
d: inner diameter of the orifice plate under operating conditions, mm;
D: inner diameter of the upstream and downstream pipes under operating conditions, mm;
ε: expansibility coefficient, dimensionless;
Δp: differential pressure across the orifice plate, Pa;
$\rho_1$: density of the fluid under operating conditions, kg/m³.

In this embodiment, a differential pressure flowmeter that is the tested instrument is calibrated with the instrument calibration apparatus 100. Here, Δp (differential pressure across the orifice plate) is the first physical quantity, and is ascertained by detecting the pressure before the orifice plate and the pressure after the orifice plate with two pressure detection modules in this embodiment, for example; $Q_f$ (volumetric flow rate under operating conditions) is the second physical quantity; the rest physical quantities may be obtained according to environmental parameters, and the like, and may be pre-stored in the instrument calibration apparatus 100 or inputted via the equation editor interface. For example, the data of the physical quantities may be as follows:

c: 0.606209;
β: 0.542035;
d: 0.044417 m;
D: 0.08194489 m;
ε: 1.000000;
$\rho_1$: 911.9927 kg/m³.

When the data is substituted into the above equation 2, the result is $Q_f$=46.019$\sqrt{\Delta p}$ (cm³/s). At the time of calibration, the instrument calibration apparatus 100 is connected with the differential pressure flowmeter that is the tested instrument through a well-known pipeline. Then, the user designates volumetric flow rate Q as the name of the second physical quantity to be measured by the tested instrument, and the instrument calibration apparatus 100 performs calibration in measurement mode according to the flow diagrams shown in FIGS. 3 and 4. As the fluid flows, the instrument calibration apparatus 100 detects the pressure before the orifice plate and the pressure after the orifice plate, obtains the value of $Q_f$ that is the second physical quantity with the above equation 2, and displays the value on the display unit 40; the value is compared with the tested (indicated) value of the differential pressure flowmeter, and thereby whether the differential pressure flowmeter has error is judged for calibration.

In this embodiment, the differential pressure flowmeter can be calibrated in real time with the instrument calibration apparatus 100 that may be used as a universal instrument. Compared with the prior art, not only real-time calculation and calibration can be realized, but also technical effects of expanding the application domain of the universal instrument and reducing the calibration cost are attained, since a special-purpose flowmeter for calibration can be omitted.

While the instrument calibration apparatus 100 is used in this embodiment to calibrate a differential pressure flowmeter that is taken as the tested instrument, the present invention is not limited to that embodiment. In addition to calibrating a differential pressure flowmeter that is taken as the tested instrument, it is obvious that the instrument calibration apparatus 100 can also be used as a differential pressure flowmeter to measure flow rate directly. Since the instrument calibration apparatus can be used in replacement of a special-purpose differential pressure flowmeter to measure flow rate, technical effects of expanding the application domain of the universal instrument and reducing the measurement cost can be attained.

Embodiment 2: Example of Calibration Application to Optical Interferometric Methane Concentration Analyzer (Calibration in (Pressure) Output Mode)

An optical interferometric methane analyzer is a portable instrument that quantitatively analyzes gas composition by measuring the change of the refractive index of the gas. The measurement range mainly includes (0~10)% $CH_4$ and (0~100)% $CH_4$. A (0~10)% $CH_4$ analyzer is used at coal mine downhole locations where the volume fraction of methane in the air is lower than 10% $CH_4$. A (0~100)% $CH_4$ analyzer is used at coal mine downhole locations where the volume fraction of methane in the air is higher than 10% $CH_4$. The analyzer is mainly composed of electrical circuit system, optical path system, and gas circuit system, and the like.

The analyzer uses a pressure method for detection. According to the working principle of the analyzer, when there is no methane gas in the measured environment, the methane chamber and the air chamber of the measuring device are filled with air, the refractive index and the optical path are the same, and the interference fringes in the analyzer have no displacement. When there is methane gas in the measured environment, the refractive index will change due to the change of the gas composition in the methane chamber, and the optical path in the methane chamber will also change, and the interference fringes will displace. The displacement of the interference fringes is proportional to the volume fraction of methane. The volume fraction of methane in the air can be obtained by measuring the displacement. In the case that both the methane chamber and the air chamber are filled with air, the refractive index of the air and the optical path in the methane chamber will also change and the interference fringes will also displace when the pressure in the methane chamber is changed. The displacement of the interference fringes is proportional to the pressure in the methane chamber. Under certain temperature conditions, the volume fraction of methane and the pressure that cause the same displacement of the interference fringes meet the conversion relation in equation 3.

$$P=x \cdot 1.7665 \cdot (273+t) \qquad \text{(equation 3)}$$

Where, x: volume fraction of methane corresponding to pressure P, % $CH_4$;
P: pressure corresponding to x % $CH_4$ volume fraction of methane in the analyzer at ambient temperature t, Pa;
t: environmental temperature, ° C.

In this embodiment, a methane concentration analyzer as a tested instrument is calibrated with the instrument calibration apparatus 100. Here, x (volume fraction of methane corresponding to pressure P) is the second physical quantity, P is the pressure calculated inversely with the equation 3 and to be outputted, i.e., the first physical quantity, and t (environmental temperature) is a parameter or the first physical quantity. The above equation 3 may be pre-stored in the instrument calibration apparatus 100, or may be edited via the equation editor interface of the man-machine interaction unit 60.

When calibration is performed with the instrument calibration apparatus 100, calibration in output mode is performed according to the flow diagrams in FIGS. 3 and 5. The user may input (write) the x % $CH_4$ volume fraction of methane (percentage) manually, and the instrument calibration apparatus 100 automatically calculates the value P (pressure value) from x with the equation 3, and starts to supply the pressure automatically to the methane concentration analyzer. When the pressure is stabilized, the tested value or indicated value of the tested instrument is compared with the standard value of the instrument calibration apparatus 100, and then the error of the tested instrument is evaluated.

Error calculation equation: error=(indicated value of the tested instrument)−(standard value). Please see "JJG 677-2006—Optical Interferometric Methane Tester" and "JJG 1040-2008—Digital Calibrator for Optical Interferometric Methane Tester" for the allowable error range of the indicated value.

The following Table 1 shows the test data obtained by testing the optical interferometric methane analyzer at 20° C. environmental temperature.

TABLE 1

| Standard value | | Indicated value of tested instrument (% CH$_4$) | | | | Error of indicated value % CH$_4$ |
|---|---|---|---|---|---|---|
| Volume fraction of methane (% CH$_4$) | Pressure (kPa) | 1 | 2 | 3 | Average | |
| 0 | 0 | 0.2 | 0.3 | 0.2 | 0.2 | 0.2 |
| 25 | 12.94 | 25.6 | 25.7 | 25.8 | 25.7 | 0.7 |
| 50 | 25.88 | 51.1 | 51.3 | 51.5 | 51.3 | 1.3 |
| 75 | 38.82 | 76.8 | 76.4 | 77.0 | 76.7 | 1.7 |
| 100 | 51.76 | 99.4 | 102.2 | 101.8 | 101.1 | 1.1 |

In Table 1, the volume fraction of methane (% CH$_4$) in the column Standard Value is a set value via the instrument calibration apparatus 100 (the second physical quantity), and the pressure (kPa) is a pressure value calculated from the % CH$_4$ value with the equation, i.e., the value supplied to the tested instrument; the indicated value of the tested instrument (% CH$_4$) is the value indicated by the tested instrument when the instrument calibration apparatus 100 supplies the calculated pressure (kPa) to the tested instrument, and the error of the indicated value is a difference between the set standard value of volume fraction of methane (% CH$_4$) and the indicated value of the tested instrument. The error of the optical interferometric methane analyzer can be evaluated according to the test data, and then the analyzer can be calibrated.

In the embodiment 2, measurement and calibration can be performed in real time for the optical interferometric methane analyzer. Compared with the prior art, the instrument calibration apparatus attains technical effects of real-time calculation, real-time adjustment, and real-time calibration. Furthermore, since the optical interferometric methane analyzer can be calibrated with the instrument calibration apparatus 100 that is used as a universal instrument, especially, since the calibration can be performed with the pressure generated and outputted by the instrument calibration apparatus 100, technical effects of expanding the application domain of the universal instrument and reducing the calibration cost are attained.

While the calibration is performed at 20° C. environmental temperature with parameter t in the embodiment 2, the present invention is not limited to that embodiment. The present invention can also be implemented with the instrument calibration apparatus 100 in a case that the quantity t is the first physical quantity (i.e., a variable). In that case, simply the physical quantity measurement unit 20 of the instrument calibration apparatus 100 has to be equipped with a temperature measurement unit to detect the environmental temperature in real time. While the volume fraction of methane (x) is a percentage inputted by the user in the above embodiment, the present invention is not limited to that embodiment. Alternatively, when the user instructs to calibrate the methane analyzer that is taken as the tested instrument, the control unit 60 may control the instrument calibration apparatus 100 to automatically generate a plurality of corresponding pressure values P sequentially according to the pre-stored equation 3, for example, within a range of (0~100)% CH$_4$, to perform calibration in (pressure) output mode.

Embodiment 3: Example of Calibration Application to Valve Position Indicator (Calibration in (Current) Output Mode)

Valves are control components in fluid transport systems, and have flow cut-off, regulation, diversion, counter-flow prevention, pressure stabilization, branching, or overflow pressure relief function, and the like. There are various kinds and sizes of valves for fluid control systems, ranging from the simplest stop valves to extremely complex valves used in automatic control systems. Valves can be used to control the flow of various types of fluids, such as air, water, steam, various corrosive media, mud, oil products, liquid metals, and radioactive media, and the like.

Valve position indicators are usually used together with valves to indicate valve opening (opening angle or percentage). A valve in an automatic control system comprises an I/P converter (current/pressure converter), a driving air source, an actuator, and a valve body, and the like. The valve position indicator receives external control signals (usually (4~20) mA current signals) to control valve opening.

Hereinafter an application of the instrument calibration apparatus 100 to calibration of a valve position indicator will be described.

The relation between valve opening d and current C inputted to the valve meets the following equation 4.

$$C = \frac{(d - d_{0\%})}{(d_{100\%} - d_{0\%})} \cdot (I_{100\%} - I_{0\%}) + I_{0\%} \quad \text{(equation 4)}$$

Where, d: valve opening (degree);
C: current inputted to the valve (mA);
$I_{0\%}$: lower limit of current signal inputted to the valve (mA);
$I_{100\%}$: upper limit of current signal inputted to the valve (mA);
$d_{0\%}$: lower limit of valve opening angle (degree);
$d_{100\%}$: upper limit of valve opening angle (degree).

In this embodiment, a valve position indicator that is taken as a tested instrument is calibrated with the instrument calibration apparatus 100 by calibration in output mode according to the flow diagrams in FIGS. 3 and 5. Here, C (current inputted to the valve, mA) is the first physical quantity, and is generated and outputted by the instrument calibration apparatus 100, d (valve opening, degree) is the second physical quantity, and the rest physical quantities may be obtained according to environmental parameters, and the like, i.e., they may be pre-stored in the instrument calibration apparatus 100 or inputted via the equation editor interface of the man-machine interaction unit. A valve position indicator model 5299 from Valworx is taken as the tested instrument in this embodiment.

TABLE 2

| Standard value | | Indicated value of tested instrument (degree) | Error of indicated value (degree) |
|---|---|---|---|
| Valve opening (degree) | Current (mA) | | |
| 0.0 | 4.0 | 0.0 | 0.0 |
| 18.0 | 7.6 | 17.8 | −0.2 |

TABLE 2-continued

| Standard value | | Indicated value of | Error of |
|---|---|---|---|
| Valve opening (degree) | Current (mA) | tested instrument (degree) | indicated value (degree) |
| 36.0 | 10.4 | 35.8 | −0.2 |
| 54.0 | 13.6 | 53.7 | −0.3 |
| 72.0 | 16.8 | 71.8 | −0.2 |
| 90.0 | 20.0 | 89.9 | −0.1 |

In Table 2, the valve opening (degree) in the column Standard Value is a set value via the instrument calibration apparatus 100 (a standard value of the second physical quantity); and the current (mA) is a current value calculated from the set standard value of valve opening with the equation, i.e., output value supplied to the tested instrument; the indicated value (degree) of the tested instrument is the value indicated by the tested instrument when the instrument calibration apparatus 100 supplies current corresponding to the calculated current value to the tested instrument; the error of the indicated value is the difference between the set standard value of valve opening and the indicated value of the tested instrument. The valve opening as the standard value of the second physical quantity may be set by the user via the man-machine interaction unit or may be set by the instrument calibration apparatus 100 sequentially under the control of the control unit 60 according to the pre-stored equation 4 within the range of the upper limit and lower limit of valve opening angle.

Thus, it is easy to calculate the relationship between the current inputted to the valve position indicator and the opening angle. The valve position indicator drives the valve actuator and displays the current valve opening angle when the instrument calibration apparatus 100 outputs a corresponding current signal. The valve position indicator may be tested and calibrated by comparing the calibrated output signal (standard signal) with the indicated angle of the tested valve. The error of the valve position indicator may be evaluated according to the test data in Table 2, and thereby calibration can be performed.

In the above embodiment 3, the user only has to pre-store a corresponding conversion equation in the instrument calibration apparatus 100 or input the conversion equation before the calibration, and set the standard value of the second physical quantity in the calibration process. Therefore, the instrument calibration apparatus 100 is simple and easy to operate, and can present the final value of physical quantity more intuitively when compared with traditional calibration apparatuses, it is unnecessary to perform cumbersome manual conversion at each calibration point. In addition, the instrument calibration apparatus 100 has high reusability and high working efficiency; specifically, the user only has to input the correct equation once, and then any repeated input is unnecessary. Furthermore, since the valve position indicator can be calibrated with the instrument calibration apparatus 100 that is used as a universal instrument, especially, since the calibration can be performed with the current generated and outputted by the instrument calibration apparatus 100, technical effects of expanding the application domain of the universal instrument and reducing the calibration cost are attained.

While one or more embodiments are set forth in the above description of embodiments, the structures and connections of the components in the embodiments are not limited to those described above. Any equivalent variation or modification made on the basis of the technical scheme of the present invention shall be deemed as falling in the scope of the present invention disclosed herein.

INDUSTRIAL APPLICABILITY

The instrument calibration apparatus and the calibration method provided in the present invention incorporate a measurement mode for multiple variables, are widely applicable to calibration of field instruments or instruments for industrial automation processes, and are suitable for industrial manufacturing and application.

The invention claimed is:

1. An instrument calibration apparatus, comprising:
a physical quantity input/output unit capable of inputting and outputting at least one first physical quantity;
a physical quantity measurement unit configured to measure a value of said at least one first physical quantity inputted from the physical quantity input/output unit;
a physical quantity configuration unit configured to generate a value of at least one second physical quantity from the value of said at least one first physical quantity through operations, or generate a value of said at least one first physical quantity from a value of at least one second physical quantity through operations;
a display unit configured to at least display a name and the value of the second physical quantity;
a man-machine interaction unit configured to enable a user to manipulate the instrument calibration apparatus;
a storage unit configured to store data required by the instrument calibration apparatus; and
a control unit configured to perform control to execute a first mode in a case where a physical quantity to be measured is the second physical quantity and it is unnecessary for the instrument calibration apparatus to generate and output a standard value of said at least one first physical quantity to realize the measurement, or execute a second mode in a case where a physical quantity to be measured is the second physical quantity and it is necessary for the instrument calibration apparatus to generate and output a standard value of said at least one first physical quantity to realize the measurement, wherein,
in the first mode, the physical quantity measurement unit is controlled to measure a value of said at least one first physical quantity inputted from the physical quantity input/output unit and correlated with the second physical quantity, the physical quantity configuration unit is controlled to generate a value of the second physical quantity from the measured value of said at least one first physical quantity inputted, and the display unit is controlled to display a name and the generated value of the second physical quantity, and
in the second mode, the physical quantity configuration unit is controlled to generate a standard value of the first physical quantity from a set standard value of said at least one second physical quantity, and the physical quantity input/output unit is controlled to output the generated standard value of the first physical quantity, and the display unit is controlled to display a name and the set standard value of the second physical quantity,
wherein, the physical quantity configuration unit performs the operations on the basis of a conversion equation with which said at least one first physical quantity can be converted to said at least one second physical quantity, or a conversion equation with which said at least one second physical quantity can be converted to said at least one first physical quantity;

the first physical quantity refers to a physical quantity that can be detected or generated directly by an instrument, including pressure, temperature, humidity, and voltage and current and the second physical quantity refers to meteorological altitude, daily air leakage volume, volumetric flow rate, methane concentration, or valve opening; and wherein, the man-machine interaction unit comprises an equation editor interface through which the conversion equation can be entered and edited, and the physical quantity configuration unit performs the operations on the basis of the conversion equation determined by the user via the man-machine interaction unit.

2. The instrument calibration apparatus according to claim 1, wherein, the storage unit can store the conversion equation in advance, and can store the conversion equation entered or edited by the user;

the physical quantity configuration unit can read the conversion equation containing the name of said at least one second physical quantity from the storage unit, according to the name of said at least one second physical quantity inputted by the user via the man-machine interaction unit;

the user edits and/or selects the conversion equation via the man-machine interaction unit on the basis of the conversion equation read by the physical quantity configuration unit.

3. The instrument calibration apparatus according to claim 1, wherein, the first physical quantity comprises pressure;

the physical quantity measurement unit comprises a pressure module for measuring pressure.

4. The instrument calibration apparatus according to claim 3, further comprising a standard pressure supply unit configured to supply standard pressure, wherein, in the second mode, the standard pressure from the standard pressure supply unit is supplied to an exterior of the instrument calibration apparatus.

5. A calibration method for calibrating an instrument to be calibrated using the instrument calibration apparatus according to claim 1, comprising:

a physical quantity name designation step, in which the user designates a name of a physical quantity to be measured by the instrument to be calibrated;

a mode designation or judgment step, in which the user designates an operating mode or the instrument calibration apparatus judges whether it is necessary to output a standard value of at least one first physical quantity to perform calibration;

a first mode execution step, in which a first mode is executed in a case that the first mode is designated or it is judged that it is unnecessary to output the standard value of said at least one first physical quantity; or a second mode execution step, in which a second mode is executed in a case that the second mode is designated or it is judged that it is necessary to output the standard value of said at least one first physical quantity, wherein, the first mode execution step comprises the following steps:

a first physical quantity input step, in which said at least one first physical quantity correlated with the second physical quantity is inputted to the instrument calibration apparatus via the physical quantity input/output unit after the user determines the second physical quantity to be measured and the conversion equation to be used;

a first physical quantity measurement step, in which a value of the inputted at least one first physical quantity correlated with the second physical quantity is measured;

a second physical quantity generation step, in which a value of the second physical quantity is generated from the measured value of said at least one first physical quantity on the basis of the conversion equation; and a display step, in which the generated value of the second physical quantity and the name of the second physical quantity are displayed together on the display unit;

wherein, the second mode execution step comprises the following steps:

a step of setting a standard value of the second physical quantity, in which the user sets a standard value of the second physical quantity or instructs the instrument calibration apparatus to set a standard value of the second physical quantity automatically after the user determines the second physical quantity to be measured and the conversion equation to be used;

a step of generating a standard value of the first physical quantity, in which a standard value of the first physical quantity is generated from the standard value of the second physical quantity set in the step of setting a standard value of the second physical quantity, on the basis of the conversion equation determined by the user;

a step of outputting the first physical quantity at the standard value, in which the first physical quantity is supplied to the instrument to be calibrated according to the standard value of the first physical quantity generated in the step of generating a standard value of the first physical quantity; and a display step, in which the set standard value of the second physical quantity and the name of the second physical quantity are displayed together on the display unit.

6. The calibration method according to claim 5, further comprising:

a conversion equation search step, in which a conversion equation containing the name of the physical quantity is searched for in the storage unit according to the name of the physical quantity designated by the user, and a search result of the conversion equation and an equation editor interface are displayed on the display unit; and a conversion equation determination step, in which the user selects, edits, or enters a conversion equation via the equation editor interface, and determines the conversion equation to be used.

7. The instrument calibration apparatus according to claim 1, configured for real-time field measurement and calibration of multiple variables, provided with a handheld casing, and comprising the following units that are electrically connected:

the physical quantity input/output unit assembled on the casing and capable of inputting and outputting at least one first physical quantity, comprising at least one pressure interface, at least one current and voltage interface, a temperature interface, and a humidity interface, which are independent from each other respectively;

the physical quantity measurement unit assembled inside the casing and configured to measure a value of said at least one first physical quantity inputted from the physical quantity input/output unit, comprising a pressure module, a current and voltage module, a temperature module, and a humidity module, which are electrically connected to the corresponding interfaces in the physical quantity input/output unit respectively;

the physical quantity configuration unit configured to generate a value of at least one second physical quantity from the value of said at least one first physical quantity through operations, or generate a value of said at least one first physical quantity from a value of at least one second physical quantity through operations; the first physical quantity refers to a physical quantity that can be detected or generated directly by an instrument, including pressure, temperature, humidity, and voltage and current; and the second physical quantity refers to meteorological altitude, daily air leakage volume, volumetric flow rate, methane concentration, or valve opening;

the display unit assembled on the casing and configured to at least display a name and the value of the second physical quantity;

the man-machine interaction unit, in the form of a touchpad disposed on the display unit and configured to enable the user to manipulate the instrument calibration apparatus;

the storage unit configured to store data required by the instrument calibration apparatus; and the control unit configured to control the physical quantity input/output unit, the physical quantity measurement unit, the physical quantity configuration unit, and the display unit.

8. The instrument calibration apparatus according to claim 7, wherein, the pressure interface is a gas pipeline interface; and the current and voltage interface is a terminal block or a plug and socket connector for electrical connection.

9. The instrument calibration apparatus according to claim 7, wherein, the first physical quantity is pressure, and the physical quantity measurement unit is a pressure module for measuring pressure, wherein, the physical quantity measurement unit further comprises a standard pressure module for supplying a standard pressure; and the physical quantity input/output unit further comprises a standard pressure interface for outputting the standard pressure, wherein the standard pressure interface is in gas connection with the standard pressure module, and the standard pressure module is electrically connected to the display unit to display the standard pressure from the standard pressure module and supplies the standard pressure to the exterior via the standard pressure interface.

10. The instrument calibration apparatus according to claim 7, wherein, the storage unit can store the conversion equation in advance, and can store the conversion equation entered or edited by the user;

the physical quantity configuration unit can read the conversion equation containing the name of said at least one second physical quantity from the storage unit, according to the name of said at least one second physical quantity inputted by the user via the man-machine interaction unit; and the user edits and/or selects the conversion equation via the man-machine interaction unit on the basis of the conversion equation read by the physical quantity configuration unit.

11. The instrument calibration apparatus according to claim 7, further comprising a communication unit connected to the control unit and communicated to a remote database through a network, wherein, the communication unit is a communication program integrated in the control unit, and the control unit is provided with a network interface for accessing the network; or alternatively, the communication unit is a separate hardware module having a connecting plug coupled to the control unit and a network interface connected to the network.

12. The instrument calibration apparatus according to claim 11, further comprising an image capturing unit connected to the control unit and connected to a camera assembled on the casing, with an image recognition program embedded in the image capturing unit.

13. The instrument calibration apparatus according to claim 1, further comprising a communication unit connected to the control unit and communicated to a remote database through a network, wherein, the communication unit is a communication program integrated in the control unit, and the control unit is provided with a network interface for accessing the network; or alternatively, the communication unit is a separate hardware module having a connecting plug coupled to the control unit and a network interface connected to the network.

14. The instrument calibration apparatus according to claim 13, further comprising an image capturing unit connected to the control unit and connected to a camera assembled on a casing, with an image recognition program embedded in the image capturing unit.

\* \* \* \* \*